(12) United States Patent
Sprenger et al.

(10) Patent No.: US 8,361,530 B2
(45) Date of Patent: Jan. 29, 2013

(54) OLIGOSACCHARIDE MIXTURE

(75) Inventors: Norbert Sprenger, Savigny (CH); Francois Morgan, Rennes (FR); Rafael Berrocal, Saint-Legier (CH); Marcel Braun, Konolfingen (CH)

(73) Assignee: Nestec S.A., Vevey (CH)

( * ) Notice: Subject to any disclaimer, the term of this patent is extended or adjusted under 35 U.S.C. 154(b) by 1018 days.

(21) Appl. No.: 12/278,918

(22) PCT Filed: Feb. 9, 2007

(86) PCT No.: PCT/EP2007/051288
§ 371 (c)(1),
(2), (4) Date: Oct. 16, 2008

(87) PCT Pub. No.: WO2007/090894
PCT Pub. Date: Aug. 16, 2007

(65) Prior Publication Data
US 2009/0092729 A1    Apr. 9, 2009

(30) Foreign Application Priority Data
Feb. 10, 2006   (EP) .................................... 06101556

(51) Int. Cl.
*A23C 9/00*   (2006.01)
(52) U.S. Cl. ....................................... 426/580; 426/658
(58) Field of Classification Search .................. 426/580, 426/587, 588, 658, 800, 801
See application file for complete search history.

(56) References Cited

U.S. PATENT DOCUMENTS
2003/0129278 A1    7/2003   Stahl et al.

FOREIGN PATENT DOCUMENTS

| WO | 9843494     | 10/1998 |
|----|-------------|---------|
| WO | 0033854     | 6/2000  |
| WO | 0142263     | 6/2001  |
| WO | 03059924    | 7/2003  |
| WO | 2004002495  | 1/2004  |
| WO | 2005000040  | 1/2005  |
| WO | 2005039597  | 5/2005  |

OTHER PUBLICATIONS

Kunz et al, Biological functions of oligosaccharides in human milk, Acta Paediatr. 82:903-12, 1993.*
Neeser et al., "Quantitative Determination of Complex Carbohydrates in Bovine Milk and in Milk-Based Infant Formulas," J. Dairy Sci. vol. 74 (1991) pp. 2860-2871.
Wrodnigg et al., "The Heyns Rearrangement Revisited: An Exceptionally Simple Two-Step Chemical Synthesis of D-Lactosamine from Lactulose," Angew. Chem. Int., vol. 38, No. 6 (1999), pp. 827-828.
International Search Report dated Jul. 16, 2007, 4 pgs.
Written Opinion of the International Searching Authority dated Jul. 16, 2007, 6 pgs.

* cited by examiner

*Primary Examiner* — Leslie Wong
(74) *Attorney, Agent, or Firm* — K&L Gates LLP

(57) ABSTRACT

An oligosaccharide mixture comprising 5-70 wt % of at least one N-acetylated oligosaccharide selected from the group comprising GalN Acα1,3Galβ1,4Glc and Galβ1,6GalN Acα1,3Galβ1,4Glc, 20-90 wt % of at least one neutral oligosaccharide selected from the group comprising Galβ1, 6Gal, Galβ1,6Glβ1,4Glc Galβ1,6Galβ1,6Glc, Galβ1,Galβ1, 3Glc, Galβ1,3Galβ1,4Glc, Galβ1,6Galβ1,6Galβ1,4Glc, Galβ1,6Galβ1,3Galβ1,4Glc, Galβ1,3Galβ1,6Galβ1,4Glc and Galβ1,3Galβ1,3Galβ1,4Glc and 5-50 wt % of at least one sialylated oligosaccharide selected from the group comprising NeuAcα2,3Galβ1,4Glc and NeuAcα2,6Galβ1,4Glc; food products comprising said oligosaccharide mixture.

16 Claims, 3 Drawing Sheets

OLIGOSACCHARIDE MIXTURE

This application is a 371 of PCT/EP2007/051288 filed Feb. 9, 2007.

FIELD OF THE INVENTION

The invention relates to an oligosaccharide mixture, food products comprising said oligosaccharide mixture and processes for producing said oligosaccharide mixture.

BACKGROUND OF THE INVENTION

The human colon is colonised with a wide range of bacteria that have both positive and negative effects on gut physiology as well as having other systemic influences. Predominant groups of bacteria found in the colon include bacteroides, bifidobacteria, eubacteria, clostridia and lactobacilli. The bacteria present have fluctuating activities in response to substrate availability, redox potential, pH, $O_2$ tension and distribution in the colon. In general intestinal bacteria can be divided into species that exert either potentially harmful or beneficial effects on the host. Pathogenic effects (which may be caused by clostridia or bacteroides, for example) include diarrhoea, infections, liver damage, carcinogenesis and intestinal putrefaction. Health-promoting effects may be caused by the inhibition of growth of harmful bacteria, stimulation of immune functions, improving digestion and absorption of essential nutrients and synthesis of vitamins. An increase in numbers and/or activities of bacterial groups (such as *Bifidobacterium* and *Lactobacillus*) that may have health promoting properties is desirable.

As far as infants specifically are concerned, immediately before birth, the gastro-intestinal tract of a baby is thought to be sterile. During the process of birth, it encounters bacteria from the digestive tract and skin of the mother and starts to become colonised. Large differences exist with respect to the composition of the gut microbiota in response to the infant's feeding. The faecal flora of breast-fed infants includes appreciable populations of Bifidobacteria with some *Lactobacillus* species, whereas formula-fed infants have more complex microbiota, with Bifidobacteria, Bacteroides, Clostridia and Streptococci all usually present. After weaning, a pattern of gut microbiota that resembles the adult pattern becomes established.

Mother's milk is recommended for all infants. However, in some cases breast feeding is inadequate or unsuccessful for medical reasons or the mother chooses not to breast feed. Infant formulae have been developed for these situations.

One approach to promote the numbers and/or activities of beneficial bacteria in the colon is the addition of prebiotics to foodstuffs. A prebiotic is a non-digestible food ingredient that beneficially affects the host by selectively stimulating the growth and/or activity of one or a limited number of bacteria in the colon, and thus improves host health. Such ingredients are non-digestible in the sense that they are not broken down and absorbed in the stomach or small intestine and thus pass intact to the colon where they are selectively fermented by the beneficial bacteria. Examples of prebiotics include certain oligosaccharides, such as fructooligosaccharides (FOS) and galactooligosaccharides (GOS).

Human milk is known to contain a larger amount of indigestible oligosaccharides than most other animal milks. In fact, indigestible oligosaccharides represent the third largest solid component (after lactose and lipids) in breast milk, occurring at a concentration of 12-15 g/l in colostrum and 5-8 g/l in mature milk. Human milk oligosaccharides are very resistant to enzymatic hydrolysis, indicating that these oligosaccharides may display essential functions not directly related to their calorific value.

As the composition of human milk becomes better understood, it has also been proposed to add prebiotics to infant formula. Various infant formulas supplemented with prebiotics such as mixtures of fructooligosaccharides and galactooligosaccharides for example are commercially available. However, such mixtures approximate only roughly the mixture of oligosaccharides in human milk. Over 100 different oligosaccharide components have been detected in human milk some of which have not been so far detected in animal milks such as bovine milk at all or have been detected only in small quantities. Examples of classes of human milk oligosaccharide that are present in bovine milk and colostrum only in very small quantities or not at all are sialylated and fucosylated oligosaccharides.

US Patent Application No. 2003/0129278 describes an oligosaccharide mixture based on oligosaccharides produced from one or several animal milks which is characterized in that it comprises at least two oligosaccharide fractions which are each composed of at least two different oligosaccharides, with free lactose not pertaining thereto. The total spectrum of the oligosaccharides present in the oligosaccharide mixture differs from those present in the animal milk or animal milks from which the oligosaccharide fractions were extracted. Further a) if said oligosaccharides are extracted from only one animal milk, the proportion of neutral oligosaccharides to acidic (sialylated) oligosaccharides is 90-60: 10-40 weight %, or b) if said oligosaccharides are extracted from at least two animal milks, the oligosaccharides extracted from two different animal milks each make up 10 weight % of the total amount of oligosaccharides present in the oligosaccharide mixture.

An object of the invention is to provide an oligosaccharide mixture which is effective as a prebiotic, particularly in the human gut.

SUMMARY OF THE INVENTION

In one aspect the invention relates to an oligosaccharide mixture which comprises 5-70 wt % of at least one N-acetylated oligosaccharide selected from the group comprising GalN Acα1,3Galβ1,4Glc and Galβ1,6GalN Acα1,3Galβ1, 4Glc, 20-90 wt % of at least one neutral oligosaccharide selected from the group comprising Galβ1,6Gal, Galβ1, 6Galβ1,4Glc   Galβ1,6Galβ1,6Glc,   Galβ1,3Galβ1,3Glc, Galβ1,3Galβ1,4Glc, Galβ1,6Galβ1,6Galβ1,4Glc, Galβ1, 6Galβ1,3Galβ1,4Glc   Galβ1,3Galβ1,6Galβ1,4Glc   and Galβ1,3Galβ1,3Galβ1,4Glc and 5-50 wt % of at least one sialylated oligosaccharide selected from the group comprising NeuAcα2,3Galβ1,4Glc and NeuAcα2,6Galβ1,4Glc.

This ingredient is a new protective and immuno-modulating ingredient that is particularly effective as a prebiotic. The mixture is structurally closer to human breast milk oligosaccharides than commercially available prebiotic ingredients, such as FOS and GOS, for example in that it includes a mixture of acidic and neutral oligosaccharides.

In an embodiment the oligosaccharide mixture may be derived from animal milk, such as one or more of cows' milk, goats' milk or buffalo milk.

In another aspect the invention relates to a food product comprising an oligosaccharide mixture as described above. Optionally the food product is an infant food or formula, but the product may be any food or drink consumed by babies, infants or adults. Consumption of a food product containing such an oligosaccharide mixture as a prebiotic will selectively promote the growth and/or activity of one or a limited number of beneficial bacteria in the colon, and thus improve host health.

DETAILED DESCRIPTION OF THE INVENTION

Figure 1:
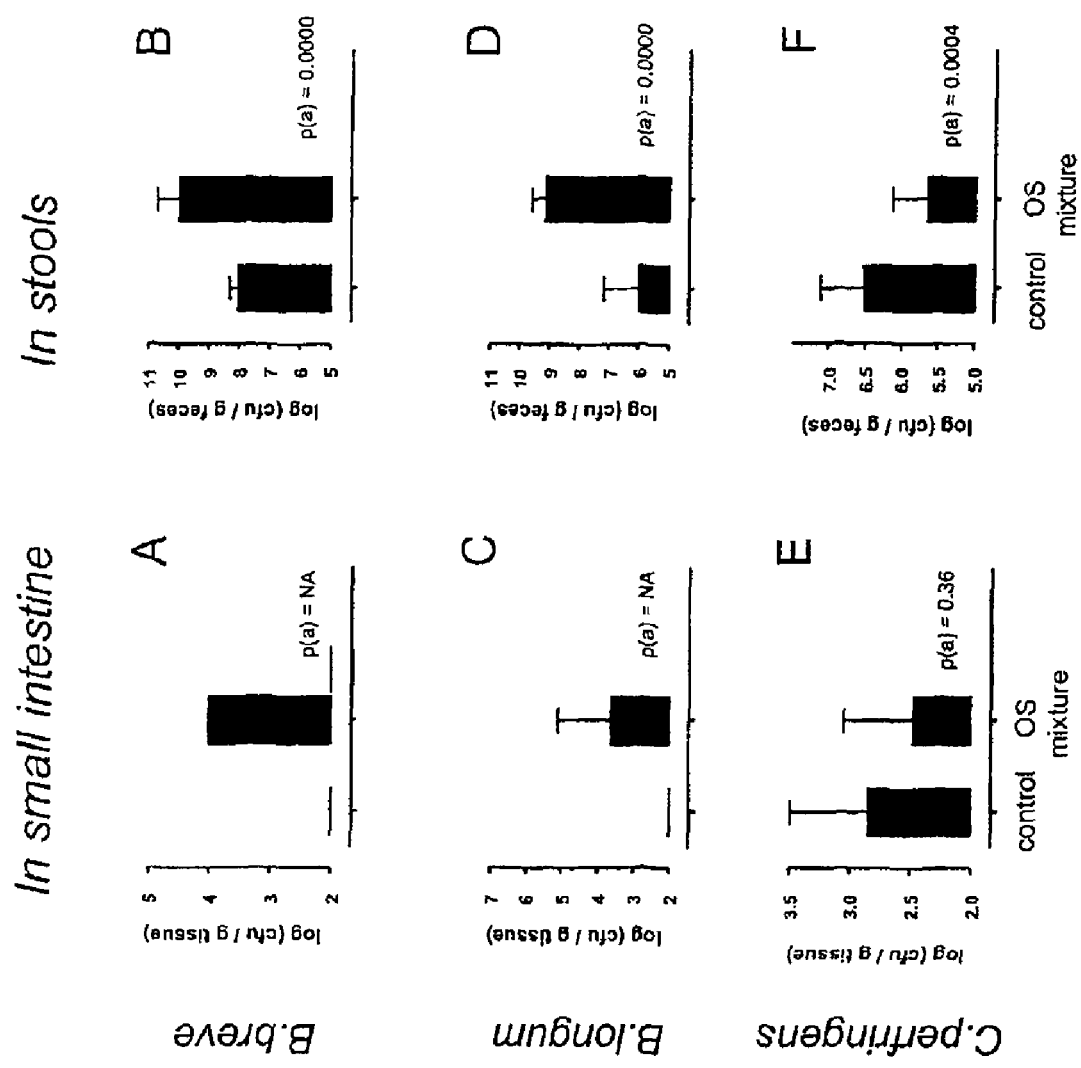
FIG. 1 shows *Bifidobacterium breve*, (A, B) *B. longum* (C, D) and *C. perfringens* (E, F) counts in the small intestine (jejunum) and stool after 2 weeks of the intervention described in Example 3. Median bacterial counts expressed as log values with robust standard deviation are represented for the control group and group with the OS mixture according to the invention. Probabilities for an effect are indicated based on robust ANOVA. (N=9 to 10). (NA, not applicable due to values below limit of detection.

In the present specification, the following words are given a definition that must be taken into account when reading and interpreting the description, examples and claims.

"Infant formula": foodstuff intended for the complete nutrition of infants during the first four to six months of life. (Article 1.2 of the European Commission Directive 91/321/EEC of 14 May 1991 on infant formulae and follow-on formulae)

It has to be understood that infants can be fed solely with infant formulae, or that an infant formula can be fed by the mother or other care-giver as a complement to human milk. The term "infant formula" as used herein is synonymous with the widely used expression "starter formula".

N-acetylated oligosaccharides: oligosaccharides having an N-acetyl residue.

Neutral oligosaccharides: those oligosaccharides which have no charge and no N-acetyl residue.

"Prebiotic": a non-digestible food ingredient that beneficially affects the host by selectively stimulating the growth and/or activity of one or a limited number of bacteria in the colon and thus improves host health. (Gibson and Roberfroid "Dietary Modulation of the Human Colonic Microbiota: Introducing the Concept of Prebiotics" J. Nutr 125:1401-1412)

"Oligosaccharide": carbohydrate having a degree of polymerisation (DP) ranging from 2 to 20 inclusive but not including lactose.

Sialylated oligosaccharides: oligosaccharides having a sialic acid residue with associated charge The invention provides an oligosaccharide mixture which comprises 5-70 wt % of at least one N-acetylated oligosaccharide selected from the group comprising GalN Acα1,3Galβ1,4Glc and Galβ1,6GalN Acα1,3Galβ1,4Glc, 20-90 wt % of at least one neutral oligosaccharide selected from the group comprising Galβ1,6Gal, Galβ1,6Galβ1,4Glc Galβ1,6Galβ1,6Glc, Galβ1,3Galβ1,3Glc, Galβ1,3Galβ1,4Glc, Galβ1,6Galβ1,6Galβ1,4Glc, Galβ1,6Galβ1,3Galβ1,4Glc Galβ1,3Galβ1,6Galβ1,4Glc and Galβ1,3Galβ1,3Galβ1,4Glc and 5-50 wt % of at least one sialylated oligosaccharide selected from the group comprising NeuAcα2,3Galβ1,4Glc and NeuAcα2,6Galβ1,4Glc and infant or adult food products comprising such an oligosaccharide mixture.

Preferably the mixture comprises 10-70 wt % of the specified N-acetylated oligosaccharide(s), 20-80 wt % of the specified neutral oligosaccharide(s) and 10-50 wt % of the specified sialylated oligosaccharide(s). More preferably the mixture comprises 15-40 wt % of the N-acetylated oligosaccharide(s), 40-60 wt % of the other neutral oligosaccharide(s) and 15-30 wt % of the sialylated oligosaccharide(s). A particularly preferred mixture is 30 wt % of the N-acetylated oligosaccharide(s), 50 wt % of the neutral oligosaccharide(s) and 20 wt % of the sialylated oligosaccharide(s).

Alternatively, the mixture may conveniently comprise 5-20 wt % of the specified N-acetylated oligosaccharide(s), 60-90 wt % of the specified neutral oligosaccharide(s) and 5-30 wt % of the specified sialylated oligosaccharide(s)

The oligosaccharide mixture of the invention may be prepared from one or more animal milks. The milk may be obtained from any mammal, in particular from cows, goats, buffalos, horses, elephants, camels or sheep.

Alternatively the oligosaccharide mixture may be prepared by purchasing and mixing the individual components. For example, synthesised galacto-oligosaccharides such as Galβ1,6Galβ1,4Glc Galβ1,6Galβ1,6Glc, Galβ1,3Galβ1,4Glc, Galβ1,6Galβ1,6Galβ1,4Glc, Galβ1,6Galβ1,3Galβ1,4Glc and Galβ1,3Galβ1,6Galβ1,4Glc and mixtures thereof are commercially available under the trade marks Vivinal® and Elix'or®. Other suppliers of oligosaccharides are Dextra Laboratories, Sigma-Aldrich Chemie GmbH and Kyowa Hakko Kogyo Co., Ltd. Alternatively, specific glycoslytransferases, such as galactosyltransferases may be used to produce neutral oligosaccharides.

The N-acetylated oligosaccharides may be prepared by the action of glucosaminidase and/or galactosaminidase on N-acetyl-glucose and/or N-acetyl galactose. Equally, N-acetyl-galactosyl transferases and/or N-acetyl-glycosyl transferases may be used for this purpose. The N-acetylated oligosaccharides may also be produced by fermentation technology using respective enzymes (recombinant or natural) and/or microbial fermentation. In the latter case the microbes may either express their natural enzymes and substrates or may be engineered to produce respective substrates and enzymes. Single microbial cultures or mixed cultures may be used. N-acetylated oligosaccharide formation can be initiated by acceptor substrates starting from any degree of polymerisation (DP) from DP=1 onwards. Another option is the chemical conversion of keto-hexoses (e.g. fructose) either free or bound to an oligosaccharide (e.g. lactulose) into N-acetylhexosamine or an N-acetylhexosamine containing oligosaccharide as described in Wrodnigg, T. M.; Stutz, A. E. (1999) Angew. Chem. Int. Ed. 38:827-828.

The sialylated oligosaccharides 3'sialyl-lactose and 6'sialyl-lactose may be isolated by chromatographic or filtration technology from a natural source such as animal milks. Alternatively, they may also be produced by biotechnology using specific sialyltransferases either by enzyme based fermentation technology (recombinant or natural enzymes) or by microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerisation (DP) from DP=1 onwards.

In a preferred aspect of the invention, the oligosaccharide mixtures described above are incorporated into a food product. In the context of the present invention, the term "food product" is intended to encompass any consumable matter. Hence, it may be a product intended for consumption by humans, in particular infant formula, follow-up formula, baby food such as infant cereals and the like. In particular, the oligosaccharide mixtures of the invention can be incorporated into infant formulas, dehydrated milk or cereal mixtures.

The food product may be prepared in any suitable manner known in the art according to the type of product and the oligosaccharide mixture of the invention may be added to the product at an appropriate stage in the manufacturing process. For example, an infant formula may be prepared by blending together the protein source, any carbohydrates other than lactose and the fat source in appropriate proportions. Emulsifiers may be added if desired. Vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture.

The liquid mixture may then be thermally treated to reduce bacterial loads. For example, the liquid mixture may be rapidly heated to a temperature in the range of about 80° C. to about 110° C. for about 5 seconds to about 5 minutes. This may be carried out by steam injection or by heat exchanger, e.g. a plate heat exchanger.

The liquid mixture may then be cooled to about 60° C. to about 85° C., for example by flash cooling. The liquid mixture may then be homogenised, for example in two stages at about 7 MPa to about 40 MPa in the first stage and about 2 MPa to about 14 MPa in the second stage. The homogenised mixture may then be further cooled to add any heat sensitive components such as vitamins and minerals. The pH and solids content of the homogenised mixture is conveniently standardised at this point.

The homogenised mixture is transferred to a suitable drying apparatus, such as a spray drier or freeze drier, and converted to powder. The powder should have a moisture content of less than about 5% by weight.

The oligosaccharide mixture of the invention is preferably added directly to infant formula by dry mixing. However, if it has been prepared from an animal milk, for example as described below, it may be convenient to add the oligosaccharide mixture without first removing all the lactose. As infant formula contains a carbohydrate component which is often wholly or partially constituted by lactose, it will be apparent to the person skilled in the art that the amount of carbohydrate in the infant formula will need to be adjusted to take into account the additional carbohydrate that will be provided by the oligosaccharide mixture. The final concentration of the oligosaccharide mixture in the baby or infant food product or formula is preferably from 0.3 to 4%, preferably 0.75 to 1.54% by weight of dry matter. This corresponds to a concentration of from 0.2 to 5 grams per liter of reconstituted formula, preferably 1 to 2 g/l. However, these amounts should not be considered as limitative and should be adapted to the target population, for example based on the weight and age or health of the baby or infant, Preferably, the formula or feed containing the oligosaccharide mixture of the invention is fed to the baby at every feed.

Alternatively, the oligosaccharide mixtures may be added to wet infant or adult food products by wet mixing. The mixture may be added to baby or infant formula at concentrations of from about 0.2 to 5 grams of oligosaccharides per liter of product However, these amounts should not be considered as limitative and should be adapted to the target population, for example based on the weight and age of the baby or infant, or the health of the specific population.

Although it is preferred to supplement food products specifically targeted towards infant or baby nutrition, it may be beneficial to supplement food products not specifically targeted, or targeted to the adult population. For example, the oligosaccharide mixtures of the invention can be incorporated into healthcare nutrition products and nutritional products for the elderly. Such food products may include milk, yoghurt, curd, cheese, fermented milks, milk-based fermented products, ice-creams, fermented cereal based products, or milk-based products, among others.

In addition to the oligosaccharide mixture of the invention, a food product such as an infant formula may comprise one or more further oligosaccharides which are added separately.

The invention will now be illustrated by reference to the following examples.

Example 1

One method of preparing an oligosaccharide mixture according to the invention will now be described by way of example only.

200,000 liters of a whey ultrafiltration permeate are pre-concentrated to 22% (w/w) total solids (TS), pasteurised at about 75° C. for about 30 seconds and then concentrated by evaporation at 60° C. to reach a TS of 59% (w/w). The liquid is cooled in a crystalliser at a rate of 2° C. per hour for a period of 24 hours to crystallise the lactose. Crystallised lactose is washed then removed by a wringer The remaining liquid (mother liquor) is clarified through a decanter. The 77000 liters at 17.7% TS obtained from the clarifier are re-concentrated by evaporation at 60° C. to reach a TS of 55% (w/w) and subject to a second lactose crystallisation step under the same conditions as before. The 29000 liters at 20.55 TS of the mother liquor thereby obtained are demineralised by a combination of electrodialysis and ion exchange in a manner known per se yielding 28500 liters of a 90% demineralised liquor at 17.3% TS. This liquor, which contains approximately 1.5 grams per liter of a mixture of about 30 wt % GalN Acα1,3Galβ1,4Glc and Galβ1,6GalN Acα1,3Galβ1,4Glc, 50 wt % of Galβ1,6Galβ1,6Glc, Galβ1,6Galβ1,4Glc and Galβ1,3Galβ1,4Glc and 20 wt % of NeuAcα2,3Galβ1,4Glc and NeuAcα2,6Galβ1,4Glc, depending upon the starting material, may either be added directly to a food product such as an infant formula or may by further concentrated in a manner known per se to those skilled in the art.

For example, the lactose remaining in the liquor may be hydrolysed into glucose and galactose and these monosaccharides may be either be removed by nanofiltration or, if desired, the galactose may be at least partially polymerised for example by the action of β-galactosidase to produce galacto-oligosaccharides which will also be retained by the nanofiltration membrane.

Example 2

An example of the composition of an infant formula containing a preparation according to the present invention is given below.

| Nutrient | per 100 kcal | per liter |
| --- | --- | --- |
| Energy (kcal) | 100 | 670 |
| Protein (g) | 1.83 | 12.3 |
| Fat (g) | 5.3 | 35.7 |
| Linoleic acid (g) | 0.79 | 5.3 |
| α-Linolenic acid (mg) | 101 | 675 |
| Lactose (g) | 11.2 | 74.7 |
| OS mixture from Example 1 (g) | 0.15 | 1.0 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (μg) | 8 | 50 |
| Se (μg) | 2 | 13 |
| Vitamin A (μg RE) | 105 | 700 |
| Vitamin D (μg) | 1.5 | 10 |
| Vitamin E (mg TE) | 0.8 | 5.4 |
| Vitamin K1 (μg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (μg) | 9 | 60 |
| Pantothenic acid (mg) | 0.45 | 3 |
| Vitamin B12 (μg) | 0.3 | 2 |
| Biotin (μg) | 2.2 | 15 |
| Choline (mg) | 10 | 67 |
| Fe (mg) | 1.2 | 8 |
| I (μg) | 15 | 100 |
| Cu (mg) | 0.06 | 0.4 |
| Zn (mg) | 0.75 | 5 |

Example 3

The effect of an oligosaccharide mixture according to the invention on the establishment and composition of the intestinal microbiota was investigated in germ free mice.

C3H mice were kept germfree until the age of 8 weeks and fed on a semi synthetic AIN diet. At Day −1 of the intervention, a single dose of a human baby microbiota cocktail was given to each mouse by gavage. The mice were divided into 2 groups and their diet was changed to an AIN diet containing for one group 1.2% (w/w) lactose as additional carbohydrate and for the other group 1.2% (w/w) lactose and 2.5% (w/w) of an oligosaccharide mixture according to the invention composed of 5% (w/w) sialyl-oligosaccharides, 5% (w/w) N-acetylated oligosaccharides and 90% (w/w) neutral oligosaccharides.

The microbiota establishment was evaluated in small intestine and stool after 14 days of intervention by plate counting *Bifidobacterium breve*, *B. longum*, and *Clostridium perfringens*. From FIG. 1 it may be seen that both resident Bifidobacteria showed increased counts in small intestine and especially in stool. On the other hand *C. perfringens* counts were reduced in small intestine and especially in stool.

Figure 2:
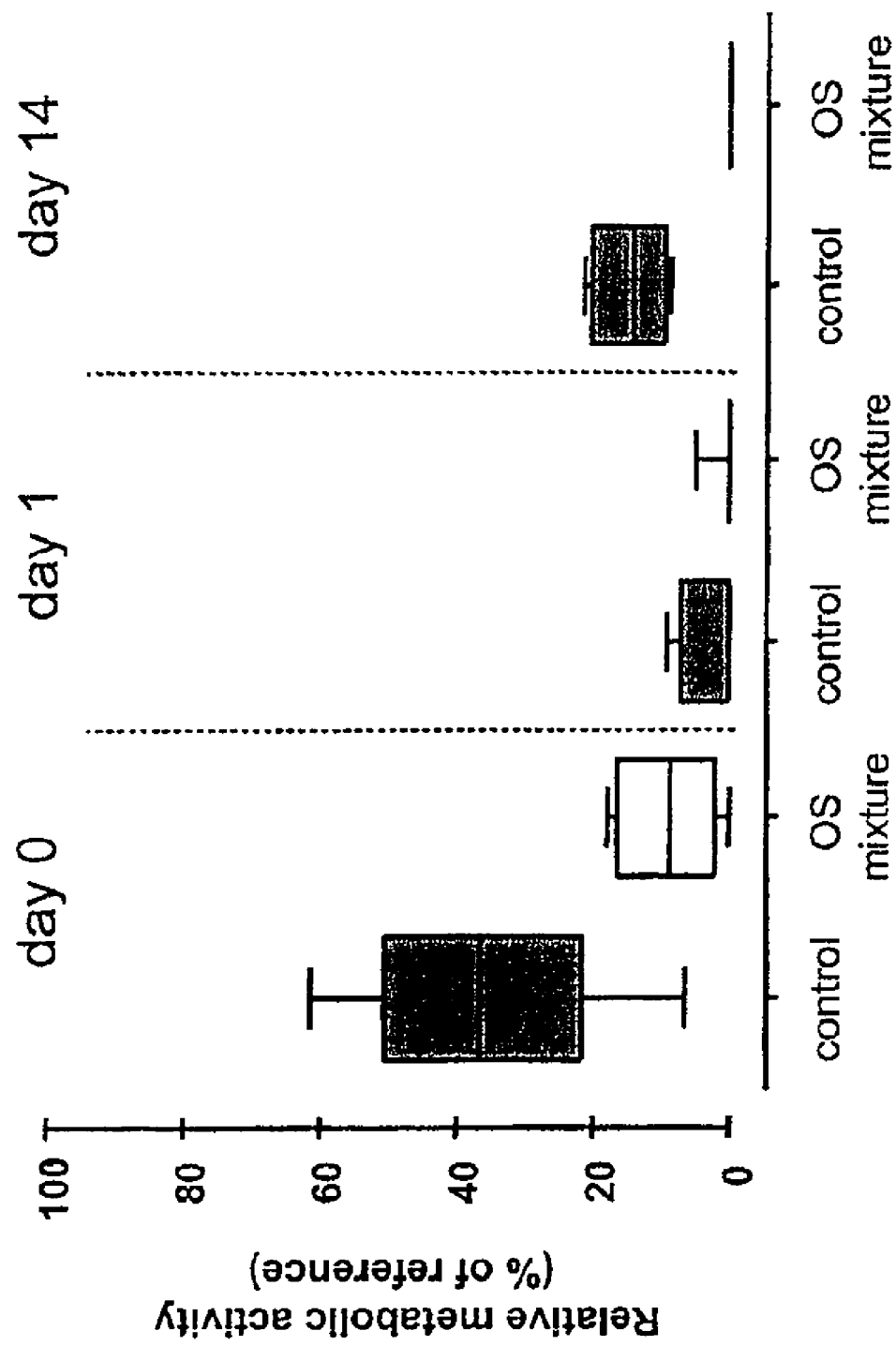
FIG. 2 shows relative overall metabolic activity of *C. perfringens* over the time of feeding of the intervention described in Example 3. Data are represented as box and whisker plot with median and interquartile range of the control group (grey boxes) and the group with the OS mixture (white boxes). (N=9 to 10). Effect of the prebiotic was significant for day 0 and day 14 as evaluated by median test involving Fisher-Exact test (p<0.005).

Over time of feeding the relative metabolic activity of *C. perfringens* was monitored by measuring levels of 16S RNA. Briefly, RNA was extracted from freshly collected faecal samples and RNA was subjected to a RT-PCR reaction to specifically amplify 16S rRNA. PCR products were separated by denaturing gradient gel electrophoresis and *C. perfringens* 16S rRNA was quantified and normalized to the *E. coli* 16S rRNA signal that remained constant during the time of feeding. As may be seen from FIG. 2 only one day after the intervention (Day 0 in FIG. 2) the metabolic activity of *C. perfringens* was considerably and significantly reduced by the OS mixture according to the invention as compared to the control group and remained lower for the duration of the intervention.

Example 4

The effect of an oligosaccharide mixture according to the invention on the establishment and composition of the intestinal microbiota was compared with the effect of neutral oligosaccharides alone in gnotobiotic mice.

C3H mice were kept germfree until the age of 6 weeks and fed on a semi synthetic AIN diet. A single dose of a human baby microbiota cocktail was given to each mouse by gavage and the microbiota was allowed to establish itself for two weeks. The mice were divided into 3 groups and their diet was changed to an AIN diet containing for the first group 1.2% (w/w) lactose as additional carbohydrate, for the second group 1.2% (w/w) lactose and 2.5% (w/w) galacto-oligosaccharides and for the third group 1.2% (w/w) lactose and 2.5% (w/w) of an oligosaccharide mixture according to the invention composed of 5% (w/w) sialyl-oligosaccharides, 5% (w/w) N-acetylated oligosaccharides and 90% (w/w) neutral oligosaccharides.

Figure 3:
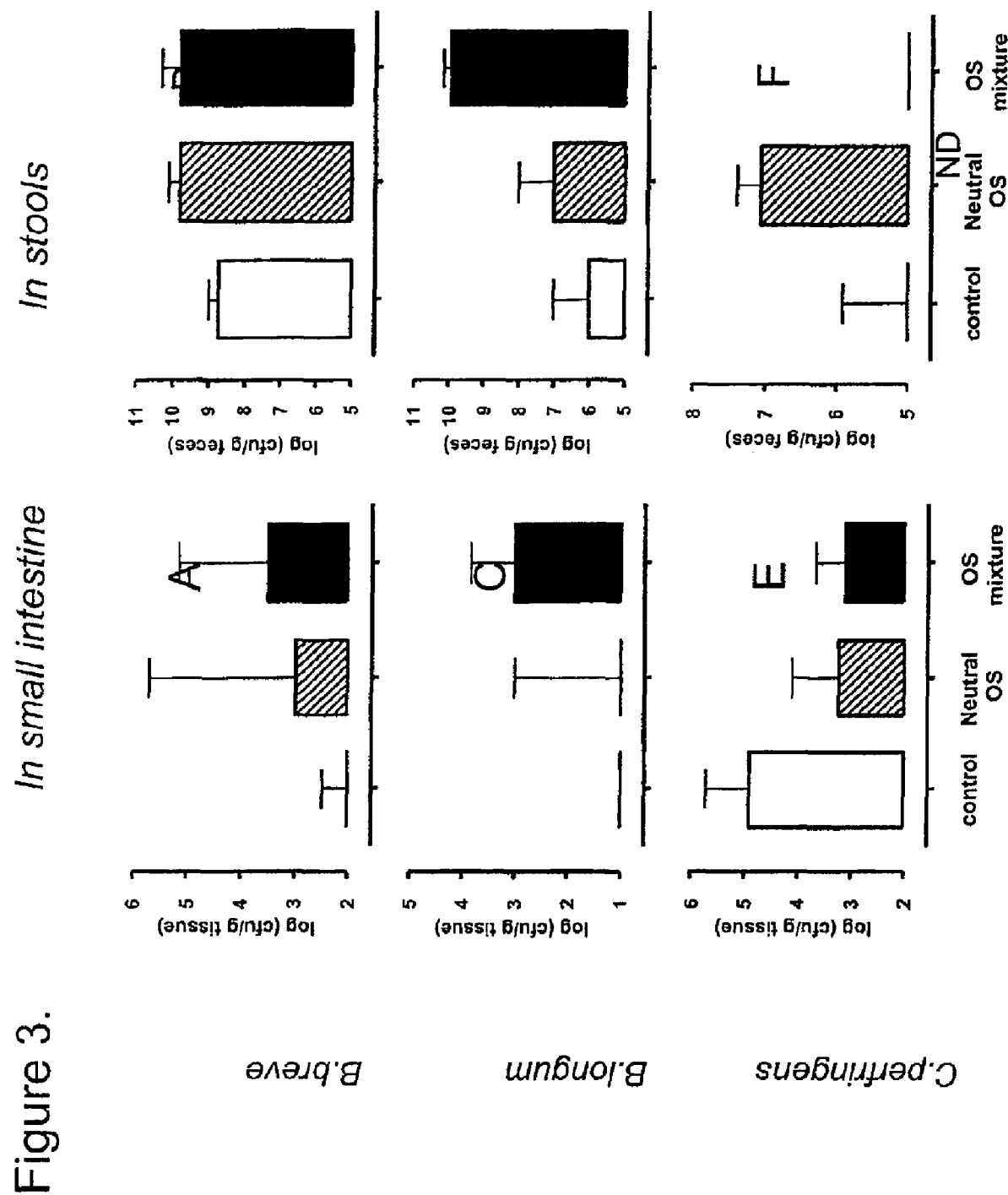
FIG. 3 shows *Bifidobacterium breve, B. longum* and *C. perfringens* counts in small intestine (jejunum) (A,C,E) and stool (B,D,F) after 2 weeks of intervention. Median of bacterial counts expressed as log values with interquartile ranges are represented for the control group, the group with neutral galacto-oligosaccharides only and the group with the oligosaccharide mixture according to the invention. ND, not detected.

The microbiota establishment was evaluated in small intestine and stool after 14 days of intervention by plate counting *Bifidobacterium breve*, *B. longum*, and *Clostridium perfringens*. From FIG. 3 it may be seen that both resident Bifidobacteria showed increased counts in small intestine and especially in stool in presence of the OS mixture in the diet. In presence of only the neutral galacto-oligosaccharides, the resident *B. longum* did not show increased counts in either small intestine or stool. *C. perfringens* counts were reduced in small intestine and also in stool in the presence of the OS mixture according to the invention. However, in presence of only the neutral galacto-oligosaccharides, increased levels of *C. perfringens* were found in stool. Together, these findings strongly suggest that the oligosaccharide mixture according to the invention has effects on microbiota balance that are superior to neutral oligosaccharides alone.

The invention claimed is:

1. An oligosaccharide mixture comprising:
    5-70 wt % of at least one N-acetylated oligosaccharide selected from the group consisting of GalN Acα1, 3Galβ1,4Glc, Galβ1,6GalN Acα1,3Galβ1,4Glc and combinations thereof;
    20-90 wt % of at least one neutral oligosaccharide selected from the group consisting of Galβ1,6Gal, Galβ1, 6Galβ1,4Glc Galβ1,6Galβ1,6Glc, Galβ1,3Galβ1,3Glc, Galβ1,3Galβ1,4Glc, Galβ1,6Galβ1,6Galβ1,4Glc; Galβ1,6Galβ1,3Galβ1,4Glc Galβ1,3Galβ1,6Galβ1, 4Glc, Galβ1,3Galβ1,3Galβ1,4Glc and combinations thereof; and
    5-50 wt % of at least one sialylated oligosaccharide selected from the group consisting of NeuAcα2,3Galβ1, 4Glc, NeuAcα2,6Galβ1,4Glc and combinations thereof.

2. The oligosaccharide mixture as claimed in claim 1 comprising 10-70 wt % of the N-acetylated oligosaccharides, 20-80 wt % of the neutral oligosaccharides and 10-50 wt % of the sialylated oligosaccharides.

3. The oligosaccharide mixture as claimed in claim 1 comprising 15-40 wt % of the N-acetylated oligosaccharides, 40-60 wt % of the neutral oligosaccharides and 15-30 wt % of the sialylated oligosaccharides.

4. The oligosaccharide mixture as claimed in claim 1 comprising 30 wt % of the N-acetylated oligosaccharides, 50 wt % of the neutral oligosaccharides and 20 wt % of the sialylated oligosaccharides.

5. The oligosaccharide mixture as claimed in claim 1 which comprises 5-20 wt % of the N-acetylated oligosaccharides, 60-90 wt % of the neutral oligosaccharides and 5-30 wt % of the sialylated oligosaccharides.

6. The oligosaccharide mixture as claimed in claim 1 which is derived from animal milk.

7. The oligosaccharide mixture as claimed in claim 6 which is derived from an animal milk selected from the group consisting of cows' milk, goats' milk and buffalo milk.

8. The oligosaccharide mixture as claimed in claim 1 which is made synthetically.

9. A food product comprising an oligosaccharide mixture comprising:
   5-70 wt % of at least one N-acetylated oligosaccharide selected from the group consisting of GalN Acα1,3Galβ1,4Glc, Galβ1,6GalN Acα1,3Galβ1,4Glc and combinations thereof;
   20-90 wt % of at least one neutral oligosaccharide selected from the group consisting of Galβ1,6Gal, Galβ1,6Galβ1,4Glc Galβ1,6Galβ1,6Glc, Galβ1,3Gal1,3Glc, Galβ1,3Galβ1,4Glc, Galβ1,6Galβ1,6Galβ1,4Glc, Galβ1,6Gal1,3Galβ1,4Glc Galβ1,3Galβ1,6Gal1,4Glc, Galβ1,3Galβ1,3Galβ1,4Glc and combinations thereof; and
   5-50 wt % of at least one sialylated oligosaccharide selected from the group consisting of NeuAcα2,3Galβ1,4Glc, NeuAcα2,6Galβ1,4Glc and combinations thereof.

10. The food product as claimed in claim 9 which is an infant formula.

11. The food product as claimed in claim 9 which comprises from 0.3 to 4% by weight based on dry matter of the oligosaccharide mixture.

12. The food product as claimed in claim 9 comprising 10-70 wt % of the N-acetylated oligosaccharides, 20-80 wt % of the neutral oligosaccharides and 10-50 wt % of the sialylated oligosaccharides.

13. The food product as claimed in claim 9 comprising 15-40 wt % of the N-acetylated oligosaccharides, 40-60 wt % of the neutral oligosaccharides and 15-30 wt % of the sialylated oligosaccharides.

14. The food product as claimed in claim 9 comprising 30 wt % of the N-acetylated oligosaccharides, 50 wt % of the neutral oligosaccharides and 20 wt % of the sialylated oligosaccharides.

15. The food product as claimed in claim 9 which comprises 5-20 wt % of the N-acetylated oligosaccharides, 60-90 wt % of the neutral oligosaccharides and 5-30 wt % of the sialylated oligosaccharides.

16. The food product as claimed in claim 9 which is derived from animal milk.

* * * * *